US012606793B2

(12) United States Patent
    Xia et al.

(10) Patent No.: US 12,606,793 B2
(45) Date of Patent: Apr. 21, 2026

(54) INDUSTRIALIZED PROTEIN PRODUCTION SYSTEM USING CARBON-CONTAINING INDUSTRIAL GAS

(71) Applicant: BEIJING SHOUGANG LANZATECH TECHNOLOGY CO., LTD., Beijing (CN)

(72) Inventors: Nan Xia, Beijing (CN); Yan Dong, Beijing (CN); Qi Chen, Beijing (CN); Wei Chao, Beijing (CN); Qingkun Song, Beijing (CN); Zhipeng Mo, Beijing (CN); Shuhuan Tong, Beijing (CN); Fangqi Zou, Beijing (CN); Chongyang Li, Beijing (CN)

(73) Assignee: BEIJING SHOUGANG LANZATECH TECHNOLOGY CO., LTD., Beijing (CN)

( * ) Notice: Subject to any disclaimer, the term of this patent is extended or adjusted under 35 U.S.C. 154(b) by 698 days.

(21) Appl. No.: 17/760,094

(22) PCT Filed: Jan. 21, 2022

(86) PCT No.: PCT/CN2022/073169
    § 371 (c)(1),
    (2) Date: Aug. 3, 2022

(87) PCT Pub. No.: WO2023/115677
    PCT Pub. Date: Jun. 29, 2023

(65) Prior Publication Data
    US 2024/0182845 A1    Jun. 6, 2024

(30) Foreign Application Priority Data

Dec. 20, 2021    (CN) .......................... 202111559296.7

(51) Int. Cl.
    *C12M 1/00*        (2006.01)
    *C12M 1/107*       (2006.01)
                       (Continued)

(52) U.S. Cl.
    CPC ............ *C12M 47/10* (2013.01); *C12M 23/36* (2013.01); *C12M 23/40* (2013.01); *C12M 33/06* (2013.01);
                       (Continued)

(58) Field of Classification Search
    None
    See application file for complete search history.

(56)             References Cited

U.S. PATENT DOCUMENTS

2013/0019577 A1*    1/2013    Gleason ................. C12M 43/00
                                                      55/385.7
2015/0024453 A1*    1/2015    Fradette ................. C12M 23/58
                                                      435/232
                       (Continued)

FOREIGN PATENT DOCUMENTS

CN        107099556 A      8/2017
CN        109055438 A      12/2018
WO    WO-2011090544 A1 *   7/2011    ............. B01D 3/001

OTHER PUBLICATIONS

Document titled CN109055438A Method and device for preparing ethyl alcohol, protein feed and natural gas by using biomass, machine translation of CN109055438A provided by Espacenet (Year: 2018).*

(Continued)

*Primary Examiner* — Holly Kipouros
(74) *Attorney, Agent, or Firm* — Syncoda LLC; Feng Ma

(57)             ABSTRACT
An industrialized protein production system using carbon-containing industrial gas includes a bacteria preparation system, a raw gas purification system, a water purification (Continued)

system, a bacteria separation system and a protein preparation system, wherein the bacteria preparation system is respectively communicated with the raw gas purification system, the water purification system and the bacteria separation system, and the protein preparation system is communicated with the bacteria separation system. By purifying the raw gas and the raw water and removing impurities from the raw gas and competing bacteria in the raw water, excellent raw materials and environment are provided for bacterial reproduction, which enable the raw gas to have high-efficiency fermentation, thereby increasing the yield of proteins.

2 Claims, 2 Drawing Sheets

(51) Int. Cl.
| | |
|---|---|
| *C12M 1/12* | (2006.01) |
| *C12M 1/32* | (2006.01) |
| *C12M 1/34* | (2006.01) |

(52) U.S. Cl.
CPC ............ *C12M 37/02* (2013.01); *C12M 41/34* (2013.01); *C12M 45/06* (2013.01)

(56) References Cited

U.S. PATENT DOCUMENTS

| | | | |
|---|---|---|---|
| 2019/0352676 A1* | 11/2019 | Senaratne | ................. C12P 7/54 |
| 2022/0049200 A1* | 2/2022 | Lee | ....................... A23N 17/007 |
| 2022/0056394 A1* | 2/2022 | Leung | .................... C12M 39/00 |
| 2023/0347287 A1* | 11/2023 | Joshi | ...................... B01D 53/85 |

OTHER PUBLICATIONS

First Office Action prepared by the State Intellectual Property Office of the P.R. China for 202111559296.7 on Mar. 8, 2023, 6 pages.

* cited by examiner

INDUSTRIALIZED PROTEIN PRODUCTION SYSTEM USING CARBON-CONTAINING INDUSTRIAL GAS

CROSS-REFERENCE TO RELATED APPLICATIONS

The present disclosure is a national stage of International Application No. PCT/CN2022/073169 filed on Jan. 21, 2022, which claims priority to Chinese Patent Application No. 202111559296.7 filed on Dec. 20, 2021. These applications are hereby incorporated by reference in their entirety.

TECHNICAL FIELD

The present disclosure relates to an industrialized protein production system using carbon-containing industrial gas and belongs to the field of protein production.

BACKGROUND OF THE INVENTION

At present, a process for preparing proteins by treating gas containing $CO/CO_2/H_2$, such as, tail gas from iron and steel industry, synthesis gas, and tail gas from refining industry, through a microbial fermentation method has been well developed due to its reduced energy consumption, safety, and high efficiency. The final products in the process include, in addition to by-product alcohols, a large number of end-of-life bacteria produced during and after the microbial fermentation. These end-of-life bacteria produce wastewater having a high concentration of bacteria proteins which can be up to 10 g/L-30 g/L. After separation and recovery treatment, a large amount of protein can be collected from the wastewater, which has a considerable economic benefit. But if the wastewater is directly discharged, it will not only lead to the loss of protein substances, but also the high-concentration protein water will have a certain impact on the environment. However, in the process for preparing protein with the existing microbial fermentation method, the growth and metabolism of bacteria are poor, and the protein yield is low.

SUMMARY

The disclosure provides an industrialized protein production system using carbon-containing industrial gas. By utilizing one or more embodiments of the disclosure, the technical problem of low yield in the process for preparing protein with the existing microbial fermentation is solved.

The disclosure provides an industrialized protein production system using carbon-containing industrial gas, which includes: a raw gas purification system for removing impurities from raw gas; a water purification system for killing competing bacteria in raw water; a bacteria preparation system communicated with the raw gas purification system and the water purification system and configured to obtain mash by taking the raw gas and the raw water as raw materials for fermentation; a bacteria separation system communicated with the bacteria preparation system and configured to separate bacteria and alcohols from the mash; and a protein preparation system communicated with the bacteria separation system and configured to prepare a bacterial protein product using the bacteria.

The disclosure provides high-quality raw materials for bacterial growth and reproduction by purifying the raw gas and the raw water and ensuring removal of impurities in the raw water, and provides an excellent environment for bacterial growth and reproduction by removing competing bacteria from the raw water, so the raw gas can ferment efficiently in the bacteria preparation system. Further, bacterial proteins having high-quality are obtained by the bacteria separation system and the protein preparation system, such that the yield of proteins is improved.

BRIEF DESCRIPTION OF THE DRAWINGS

The accompanying drawings, which are incorporated in and constitute a part of the specification, illustrate embodiments consistent with the disclosure and together with the description to explain the principles of the disclosure.

In order to illustrate the embodiments of the disclosure or the technical solutions in the prior art more clearly, accompanying drawings that need to be used in the description for the embodiments or the prior art will be briefly introduced below. It is obvious that other drawings can also be obtained by those skilled in the art based on these drawings without creative effort.

REFERENCE NUMBER

1—raw gas purification system, 111—first dust removal device, 112—second dust removal device, 121—first adsorption device, 122—electric heater, 123—second adsorption device, 124—vacuum pump, 13—raw gas temperature control device, 14—water separator;

2—water purification system, 21—gas sterilization device, 22—chemical sterilization device, 23—purified water delivery pump;

3—bacteria preparation system, 31—bacteria preparation device, 32—bacteria delivery pump, 33—bacteria concentration device;

4—bacteria separation system, 41—distillation separation device, 42—centrifugal separation device, 43—distillation bottom liquid delivery pump;

5—protein preparation system, 51—drying device, 52—packaging device.

DETAILED DESCRIPTION

In order to make the purpose, technical solutions, and advantages of the embodiments of the disclosure clearer, the technical solutions in the embodiments of the disclosure will be described clearly and completely below in conjunction with accompanying drawings therein. Obviously, the described embodiments are some, but not all, embodiments of the present disclosure. Based on the embodiments in the present disclosure, all other embodiments obtained by those of ordinary skill in the art without creative work shall fall within the protection scope of the disclosure.

Figure 1:
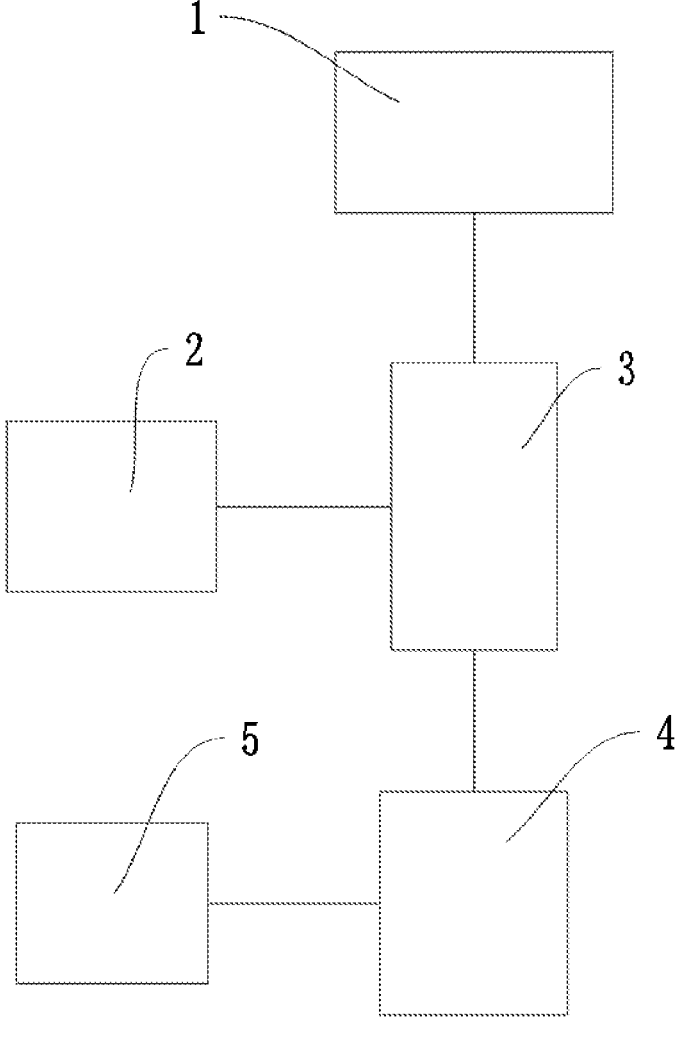
FIG. 1 is a schematic diagram of an industrialized protein production system using carbon-containing industrial gas in accordance with some embodiments of the disclosure.

The disclosure provides an industrialized protein production system using carbon-containing industrial gas as shown in FIG. 1, which may include:

a raw gas purification system 1, which is capable in removing impurities from raw gas;

a water purification system 2, which is capable in killing competing bacteria in raw water;

a bacteria preparation system 3, which is communicated with the raw gas purification system 1 and the water purification system 2, and is capable in obtaining mash by taking the raw gas and the raw water as raw materials for fermentation;

a bacteria separation system 4, which is communicated with the bacteria preparation system 3 and is capable in separating bacteria and alcohols from the mash; and a protein preparation system 5, which is communicated with the bacteria separation system 4 and is capable in preparing a bacterial protein product using the bacteria.

The raw gas purification system 1 may purify the raw gas. Meanwhile, the water purification system 2 may purify the raw water. The purified raw gas and the purified raw water are fed to the bacteria preparation system 3, in which the bacteria are fermented by taking the raw gas and raw water as raw materials to obtain the mash, and the mash contains bacteria and fermentation products such as alcohols, impurities and water. Thereafter, the mash is fed to the bacteria separation system 4, in which the bacteria and alcohols are separated from the mash and the impurities and water are discharged. The alcohols are fed to other processing systems and the bacteria are fed to the protein preparation system 5 as proteins and are prepared into the bacterial protein product which may be used as feeds for animals.

In some embodiments of the disclosure, the raw gas may include carbon-containing industrial gas and hydrogen. In some embodiments, the raw gas includes CO, $CO_2$ and $H_2$. Impurities in the raw gas, including tar, benzene series, oxygen, and halides, are removed through the raw gas purification system 1 to prevent them from affecting the growth of bacteria. Dusts are also removed from the raw gas purification system 1, which prevents them from entering the bacteria preparation system 3 and affecting the purity of the bacterial protein product. In addition, competing bacteria in the raw water, such as methane bacteria, can compete with the bacteria for carbon sources, occupy the living space of the bacteria, and affect the normal growth and reproduction of the bacteria, which, on the one hand, can lead to a decrease in the yield of protein, and a decrease in the yield of alcohol produced by fermentation, and on the other hand, can lead to decline or even death of the bacteria, so that the continuous operation time of the system cannot be guaranteed. The removal of competing bacteria in the raw water by the water purification system 2 can ensure the purity of the bacteria in the bacteria preparation system 3, improve the yield and purity of the protein, and at the same time, enable the industrialized protein production system using carbon-containing industrial gas operating efficiently for a long time.

Figure 2:
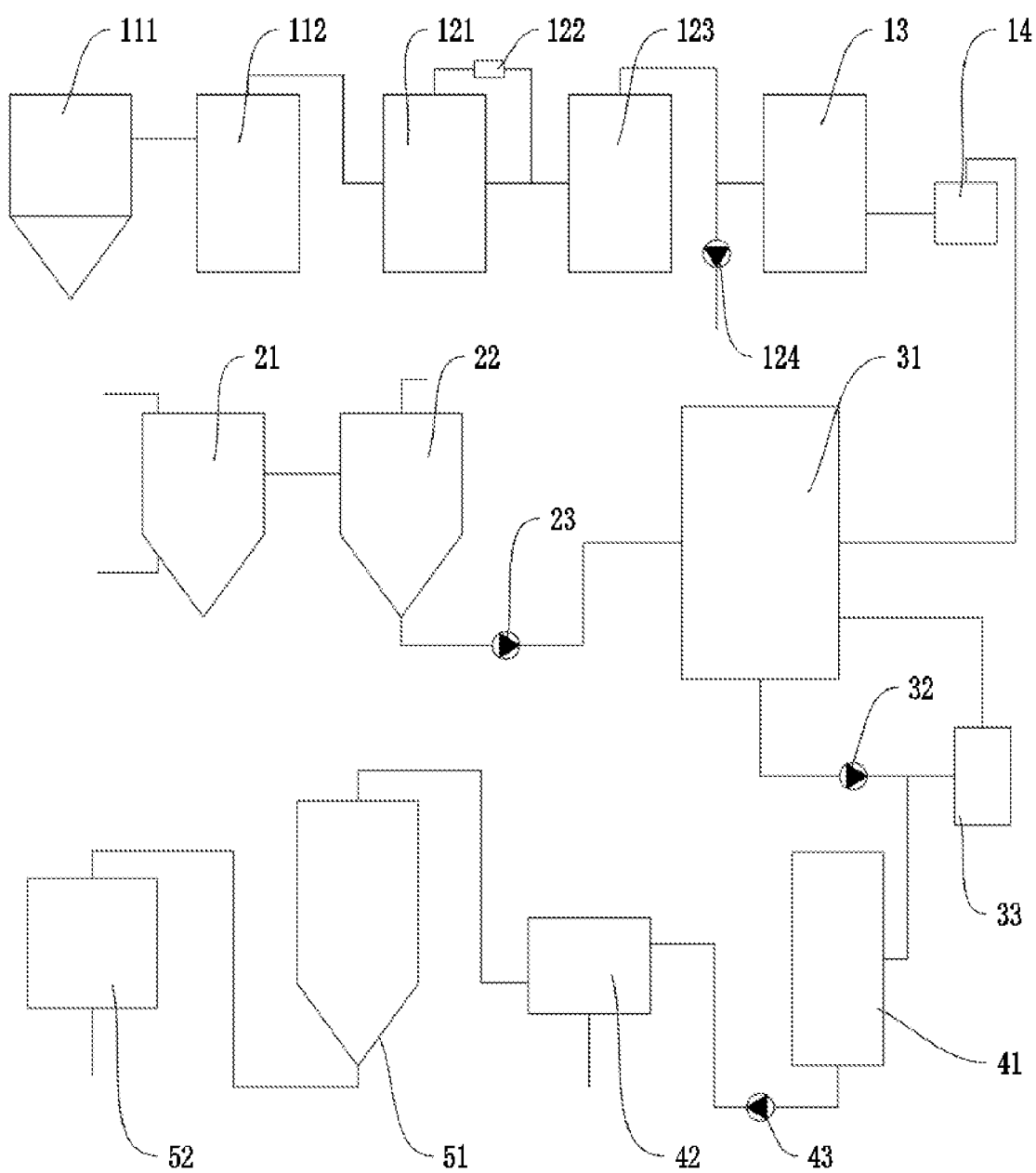
FIG. 2 is a schematic diagram of an industrialized protein production system using carbon-containing industrial gas in accordance with other embodiments of the disclosure.

In some embodiments, as shown in FIG. 2, the raw gas purification system 1 may include:

a raw gas dust removal device, which is capable in removing dusts and tar from the raw gas;

a raw gas impurity purification device, which is communicated with the raw gas dust removal device and is capable in removing benzene series, halides, and oxygen from the raw gas;

a raw gas temperature control device 13, which is communicated with the raw gas impurity purification device and is capable in controlling a temperature of the raw gas; in some embodiments of the disclosure, the raw gas temperature control device 13 may be a water cooler; and a water separator 14, which is communicated with the raw gas temperature control device 13 and the bacteria preparation system 3 and is capable in removing moisture from the raw gas.

In some embodiments of the disclosure, the raw gas dust removal device may include a first dust removal device 111 and a second dust removal device 112. The first dust removal device 111 may be a bag dust collector or a washing tower. The raw gas impurity purification device may include a first adsorption device 121, an electric heater 122 and a second adsorption device 123. The raw gas may be fed into the first dust removal device 111, in which most dust particles are removed to obtain a purified gas with a dust content <5 $mg/m^3$, next fed into the second dust removal device 112, in which dusts are further removed and tar are partially removed to obtain a purified gas with a dust content ≤1 $mg/m^3$ and a tar content ≤1 $mg/m^3$, and then fed into the first adsorption device 121 to remove benzene series impurities from the raw gas to obtain a purified gas with a benzene series content ≤0.1 ppm. Then the purified gas with the benzene series content ≤0.1 ppm may be heated by the electric heater 122 and fed into the second adsorption device 123, in which halides are removed to obtain a purified gas with a halide content ≤0.1 ppm and an oxygen content ≤1000 ppm, and then fed into the raw gas temperature control device 13 and be cooled to a temperature between 32° C.-40° C., and finally fed into a gas-liquid separation device to separate liquid state water from the raw gas. The treated raw gas may be fed into the bacteria preparation system 3 as the raw materials for fermentation.

Dust and impurities in the raw gas can be removed by the raw gas dust removal device and the raw gas impurity purification device to prevent dust from affecting the purity of the bacterial protein product, and to prevent impurities from affecting the growth and reproduction of bacteria, thereby improving the yield of bacterial proteins. Meanwhile, the temperature of the raw gas can be controlled at 32° C.-40° C. suitable for the growth of the bacteria by the raw gas temperature control device 13, so as to prevent the high or low temperature of the raw gas from affecting the reproductive efficiency of the bacteria, while lowering the temperature of the raw gas such that the gas-liquid separation device can perform gas-liquid separation.

In some embodiments of the disclosure, an outlet of the electric heater 122 can further be linked to the first adsorption device 121. When the first adsorption device 121 or the second adsorption device 123 needs to be regenerated, a regeneration gas is passed into an inlet of the electric heater 122 which increases the temperature of the regeneration gas to a regeneration temperature to improve regeneration efficiency.

A process of adsorption under an increased pressure and followed by desorption under a reduced or normal pressure is called pressure swing adsorption. Since a thermal conductivity of an adsorbent is small and a temperature of an adsorbent bed layer caused by adsorption heat and desorption heat is almost constant, the pressure swing adsorption can be regarded as an isothermal process. Its operating condition approximately follows an isotherm of ambient temperature adsorption, with adsorption at higher pressure and desorption at lower pressure. In some embodiments of the disclosure, when the first adsorption device 121 or the second adsorption device 123 is about to perform adsorption, a vacuum pump 124 can also be used to increase the pressure therein and improve the adsorption efficiency; and when the first adsorption device 121 or the second adsorption device 123 needs to be regenerated, the gas in the first adsorption device 121 or the second adsorption device 123 can also be pumped out through the vacuum pump 124 to reduce the pressure therein and improve the desorption efficiency.

In some embodiments, the water purification system 2 may include:

a gas sterilization device 21, which is communicated with the raw gas purification system 1 and is capable in passing sterilizing gas into the raw water;

a chemical sterilization device 22, which is communicated with the gas sterilization device 21 and the bacteria preparation system 3 and is capable in adding a sterilant into the raw water; and a purified water delivery pump 23, which is disposed between the chemical sterilization device 22 and the bacteria preparation system 3 and is capable in pumping purified water from the chemical sterilization device 22 into the bacteria preparation system 3.

The top of the gas sterilization device 21 is communicated with a process water inlet, and the bottom of the gas sterilization device 21 is communicated with a gas inlet, and the upper middle part of the gas sterilization device 21 is communicated with the chemical sterilization device 22 through overflow. The top of the chemical sterilization device 22 is provided with a sterilant inlet, and an outlet of the chemical sterilization device 22 is communicated with an inlet of the purified water delivery pump 23.

In some embodiments of the disclosure, the raw water is first fed into the gas sterilization device 21, and bacterial colonies in the raw water can be oxidized by passing ozone into the gas sterilization device 21. Then, the treated raw water is passed into the chemical sterilization device 22, and the bacterial colonies in the raw water can be killed thoroughly by adding a sterilant into the chemical sterilization device 22, to obtain purified water with a total count of bacterial colonies ≤1 cfu/g. In other embodiments, the raw water is sampled at an outlet of the chemical sterilization device 22 to detect a count of bacterial colonies and a sterilant content in the raw water, so as to achieve the total count of bacterial colonies ≤1 cfu/g and the sterilant content of 0.002‰-0.01‰ by mass fraction.

In some embodiments of the disclosure, the raw water is fed successively into the gas sterilization device 21 and the chemical sterilization device 22, while in other embodiments, the raw water can be first fed into the chemical sterilization device 22 and then into the gas sterilization device 21, which does not affect the implementation of the technical solutions of the disclosure.

In some embodiments, the bacteria preparation system 3 includes:

a bacteria preparation device 31, which is communicated with the raw gas purification system 1 and the water purification system 2 and is capable in obtaining the mash by taking the raw gas and the raw water as raw materials for fermentation under the action of bacteria; in an embodiment of the disclosure, inlets of the bacteria preparation device 31 are respectively communicated with an outlet of the water separator 14 and an outlet of the purified water delivery pump 23, and the bacteria preparation device 31 may be a bioreactor;

a bacteria delivery pump 32, which is communicated with the bacteria preparation device 31 and the bacteria separation system 4 and is capable in pumping the mash in the bacteria preparation device 31 into the bacteria separation system 4; and a bacteria concentration device 33, which is communicated with the bacteria delivery pump 32 and the bacteria preparation device 31 and is capable in separating the mash into thick mash and clear mash and to adjust concentration and liquid level of the mash in the bacteria preparation device 31; in an embodiment of the disclosure, the bacteria concentration device 33 may be a concentrator or a filter.

The purified gas is fed into the bacteria preparation device 31 from the outlet of water separator 14, and purified water is fed into the bacteria preparation device 31 from the outlet of purified water delivery pump 23. Ethanol is produced from the raw gas and raw water under the action of the bacteria, while the bacteria reproduce therein. The bacteria, ethanol, water and impurities are mixed as the mash, and fed to the bacteria delivery pump 32. The mash is divided into two strands when outputting from the bacteria delivery pump 32, one strand enters the bacteria separation system 4, and the other strand enters the bacteria concentration device 33. After the mash enters the bacteria concentration device 33, it is separated into thick mash and clear mash, and the thick mash is returned to the bacteria preparation device 31, which can adjust the concentration and liquid level of mash in the bacteria preparation device 31. The clear mash is fed into other processes for treatment.

When a reproduction rate of the bacteria decreases, since the mash continuously discharged from the bacteria preparation device 31 includes the bacteria and the product alcohols, it is hard for the bacteria delivery pump 32 alone to adjust the concentration of the mash in the bacteria preparation device 31. As a result, the reproduction rate of the bacteria decreases continuously. Such a vicious circle will eventually lead to a cessation of the reaction and hard to maintain a production-output equilibrium point, making the industrialized protein production system using carbon-containing industrial gas unable to operate for a long time. Therefore, according to the disclosure, the bacteria concentration device 33 is provided. When the concentration of the mash in the bacteria preparation device 31 decreases, the thick mash separated by the bacteria concentration device 33 is returned to the bacteria preparation device 31, so that the concentration of the mash in the bacteria preparation device 31 can be increased. When the concentration of the mash in the bacteria preparation device 31 increases, an efflux volume coming from the bacteria delivery pump 32, i.e., the efflux volume of the mash, can also be increased to reduce the concentration of the mash. By controlling operations of the bacteria delivery pump 32, the supply of raw water, and the amount of thick mash returned from the bacteria concentration device 33 to the bacteria preparation device 31, on the one hand, the liquid level of the mash in the bacteria preparation device 31 can be controlled, and on the other hand, high-concentration bacteria with the concentration of 3%-6% can be obtained.

In some embodiments, the bacteria separation system 4 may include:

a distillation separation device 41, which is communicated with the bacteria preparation system 3 and is capable in separating the alcohols in the mash, wherein a temperature at the bottom of the distillation separation device 41 is ≤90° C. and a pressure at the top is ≤−50 kPa, and ethanol can be obtained by distillation;

a centrifugal separation device 42, which is communicated with the distillation separation device 41 and the protein preparation system 5 and is used to separate the bacteria in the mash; in the embodiment of the disclosure, the centrifugal separation device 42 may include one or more of a disc centrifuge, a decanter centrifuge, an organic membrane or an inorganic membrane; and a distillation bottom liquid delivery pump 43, which is communicated with the centrifugal separation device

42 and is capable in feeding the distilled bottom liquid containing bacteria into the centrifugal separation device 42.

The existing protein preparation method usually directly distills the mash prepared by the bacteria preparation system 3, but water-soluble ions cannot be evaporated with water and still remain in the solid obtained after evaporation, so that a large number of impurities remains in the prepared bacterial protein product, which affects the purity of the product. In some embodiments of the disclosure, alcohols in the mash are distilled off first, and the remaining impurities, bacteria and water are fed into the centrifugal separation device 42, in which water and water-soluble impurities are separated by centrifugation to obtain the higher concentration bacteria with the concentration of 15%-30% and the yield of bacteria >95%, which are fed into the protein preparation system 5.

In some embodiments, the protein preparation system 5 comprises:

a drying device 51, which is communicated with the bacteria separation system 4 and is used to dry the bacteria to prepare bacterial proteins, wherein a drying temperature of the drying device 51 is ≤200° C.; in an embodiment of the present disclosure, the drying

Comparative Example 1

In this comparative example, the raw gas and water were not purified, the bacteria concentration device was not provided, and an evaporation concentration process was applied.

S1, directly feeding raw gas and water into a bacteria preparation system 3, to obtain low-concentration bacteria having a concentration of 1%-2% and a clear liquid;

S2, mixing and feeding the low-concentration bacteria into a distillation separation device, to obtain low-concentration bacteria having a concentration of 1.2%-2.3%;

S3, concentrating by evaporation the concentrated bacteria liquid produced by the distillation separation device, to obtain high-concentration bacteria having a concentration of 6%-10%; and S4, obtaining bacterial proteins through processes of drying and finished product packaging.

Continuous stable running time of bacteria preparation system 3, crude protein content in the bacterial proteins, ash content, yield, and steam consumption per ton of product were calculated for each of the Embodiments and Comparative Examples, as shown in Table 1.

TABLE 1

| Group | Continuous stable running time of bacteria preparation system | Crude protein content | Ash content | Yield | Protein production per 10000 Nm³ raw gas | Steam consumption per ton of product |
|---|---|---|---|---|---|---|
| Embodiment1 | >12 months | ≥85% | <1% | >95% | 1.4 t-1.8 t | 5 t-6 t |
| Comparative Example 1 | <1 month | 65%-75% | 8%-10% | 80%-85% | 0.8 t-1 t | 10 t-15 t | device may comprise one or more of spray drying, pressure drying, fluid bed drying and roller blade drying; and a packaging device 52, which is communicated with the drying device 51 and is capable in packaging the bacterial proteins into a bacterial protein product.

In some embodiments of the disclosure, in order to prevent the proteins from being decomposed at high temperature, the drying temperature of the drying device 51 is set to be less than or equal to 200° C.

The industrialized protein production system using carbon-containing industrial gas of the disclosure will be described in detail below with reference to the embodiments, comparative examples and experimental data.

Example 1

S1, obtaining a purified gas with a dust content ≤1 mg/m³, a halide content ≤0.1 ppm, a temperature of 32° C.-40° C. and without liquid water;

S2, obtaining a purified water with a total count of bacterial colonies ≤1 cfu/g;

S3, obtaining high-concentration bacteria having a concentration of 3%-6%;

S4, obtaining higher-concentration bacteria having a concentration of 15%-30%, with a bacteria yield of >95%; and S5, obtaining bacterial proteins through processes of drying and finished product packaging.

As can be seen from the data of Table 1, regarding the Comparative Example 1 where the raw gas and water were directly passed into the bacteria preparation system 3, the bacteria concentration device was not provided, and the concentrated bacteria liquid produced by the distillation separation device was concentrated by evaporation, the continuous stable running time of the bacteria preparation system 3 was less than 1 month; the quality of the proteins was low, with a crude protein content of 65%-75% and a high ash content of 8%-10%; the overall yield of the proteins was 80%-85%; and the protein production and the steam consumption were about 50% those of the Embodiment 1.

The industrialized protein production system using carbon-containing industrial gas provided in disclosure provides high-quality raw materials for bacterial growth and reproduction by purifying the raw gas and the raw water and removing impurities from the raw gas, and provides an excellent environment for bacterial growth and reproduction by removing competing bacteria from the raw water, so the raw gas can ferment efficiently in the bacteria preparation system 3 and obtain bacterial proteins having high-quality by using the bacteria separation system 4 and the protein preparation system 5. The proteins produced have a high quality, with a crude protein content ≥85% and an ash content ≤1%. In addition, the concentration of bacteria in the bacteria preparation system 3 is 3%-6%, and the production is significantly increased. Meanwhile, the yield of the bacterial proteins is >95% and the protein loss is reduced.

Moreover, the continuous stable running time of the bacteria preparation system 3 is >12 months and has a high overall efficiency.

It should be noted that, relational terms such as "first" and "second" as used herein are only used to distinguish one entity or operation from another entity or operation, and do not necessarily require or imply that there is any such actual relationship or order between these entities or operations. Moreover, the terms "including", "comprising" or any other variation thereof are intended to encompass non-exclusive inclusion such that a process, method, article or device comprising a series of elements includes not only those elements, but also other elements not expressly listed, or elements inherent to such a process, method, article or device. Without further limitation, an element defined by the phrase "comprising a . . . " does not preclude the presence of additional identical elements in a process, method, article or device that includes the element.

The above are only specific embodiments of the disclosure for enabling those skilled in the art to understand or implement the disclosure. Various modifications to these embodiments will be readily apparent to those skilled in the art, and the generic principles defined herein may be implemented in other embodiments without departing from the spirit or scope of the disclosure. Thus, the disclosure is not intended to be limited to the embodiments shown herein, but is to be accorded the widest scope consistent with the principles and novel features claimed herein.

The invention claimed is:

1. An industrialized protein production system using carbon-containing industrial gas, comprising:

a raw gas purification apparatus configured to remove impurities from raw gas;

a water purification apparatus configured to kill competing bacteria in raw water;

a bacteria preparation apparatus communicative with the raw gas purification apparatus and the water purification apparatus and configured to obtain mash by taking the raw gas and the raw water as raw materials for fermentation;

a bacteria separation apparatus communicative with the bacteria preparation apparatus and configured to separate bacteria and alcohol from the mash; and a protein preparation apparatus communicative with the bacteria separation apparatus and configured to prepare a bacterial protein product through the bacteria;

wherein the raw gas purification apparatus comprises:

a raw gas dust removal device configured to remove dust and tar from the raw gas;

a raw gas impurity purification device communicative with the raw gas dust removal device and configured to remove benzene series, oxygen and halides from the raw gas;

a raw gas temperature control device communicative with the raw gas impurity purification device and configured to control a temperature of the raw gas; and a water separator communicative with the raw gas temperature control device and the bacteria preparation apparatus and configured to remove moisture from the raw gas;

wherein the water purification apparatus comprises:

a gas sterilization device communicative with the raw gas purification apparatus and configured to pass sterilizing gas into the raw water;

a chemical sterilization device communicative with the gas sterilization device and the bacteria preparation apparatus and configured to add a sterilant to the raw water;

a purified water delivery pump between the chemical sterilization device and the bacteria preparation apparatus and configured to pump purified water from the chemical sterilization device into the bacteria preparation apparatus;

wherein the bacteria preparation apparatus comprises:

a bacteria preparation device communicative with the raw gas purification apparatus and the water purification apparatus and configured to obtain the mash by taking the raw gas and the raw water as the raw materials for fermentation under action of the bacteria; wherein the bacteria preparation device is a bioreactor;

a bacteria delivery pump communicative with the bacteria preparation device and the bacteria separation apparatus and configured to pump the mash in the bacteria preparation device into the bacteria separation apparatus; wherein inlets of the bacteria preparation device are respectively communicative with an outlet of the water separator and an outlet of the purified water delivery pump; and a bacteria concentration device communicative with the bacteria delivery pump and the bacteria preparation device and configured to separate the mash into thick mash and clear mash, and to adjust concentration and liquid level of the mash in the bacteria preparation device; wherein the bacteria concentration device is a concentrator or a filter;

wherein the bacteria delivery pump is configured to output two streams of the mash, wherein one stream enters the bacteria separation apparatus, and another stream enters the bacteria concentration device;

wherein the bacteria concentration device is further configured to, when a concentration of the mash in the bacteria preparation device decreases, return the thick mash to the bacteria preparation device to increase the concentration of the mash in the bacteria preparation device;

the bacteria delivery pump is further configured to, when the concentration of the mash in the bacteria preparation device increases, increase an efflux volume of the mash coming from the bacteria delivery pump to reduce the concentration of the mash;

wherein the bacteria separation apparatus comprises:

a distillation separation device communicative with the bacteria preparation apparatus and configured to separate the alcohol in the mash; wherein a temperature at a bottom of the distillation separation device is ≤90° C. and a pressure at a top of the distillation separation device is ≤−50 kPa; and a centrifugal separation device communicative with the distillation separation device and the protein preparation apparatus and configured to separate the bacteria in the mash; and a distillation bottom liquid delivery pump communicative with the centrifugal separation device and configured to feed distilled bottom liquid containing the bacteria into the centrifugal separation device;

wherein the protein preparation apparatus comprises:

a drying device communicative with the bacteria separation apparatus and configured to prepare bacterial proteins by drying the bacteria; and a packaging device communicative with the drying device and configured to package the bacterial proteins into a bacterial protein product.

2. The system of claim 1, wherein a drying temperature of the drying device is ≤200° C.

\* \* \* \* \*